United States Patent [19]
Moore

[11] Patent Number: 5,387,412
[45] Date of Patent: Feb. 7, 1995

[54] 1,2-PROPYLENE GLYCOL SHAVING SOLUTION AND METHOD OF USE THEREOF

[76] Inventor: Milton D. Moore, P.O. Box 300445, Houston, Tex. 77230-0445

[21] Appl. No.: 102,315

[22] Filed: Aug. 3, 1993

Related U.S. Application Data

[63] Continuation of Ser. No. 573,465, Aug. 27, 1990, abandoned.

[51] Int. Cl.⁶ .......................... A61K 7/15; A61K 7/06
[52] U.S. Cl. ...................................... 424/73; 424/70.1
[58] Field of Search ...................................... 424/73, 70

[56]         References Cited
         U.S. PATENT DOCUMENTS 3,472,940  10/1969  Osipow et al. ........................ 424/73
3,715,942   2/1973  Courtney ............................... 424/73
4,831,023   5/1989  Garlen et al. ......................... 514/169
4,944,939   7/1990  Moore ................................... 424/73

OTHER PUBLICATIONS

Remingtons' Pharmaceutical Science, Mack Publishing Co: 1990; p. 1317.

*Primary Examiner*—Gollamudi S. Kishore
*Assistant Examiner*—James M. Spear
*Attorney, Agent, or Firm*—Conley, Rose & Tayon

[57]            ABSTRACT

Disclosed is a hydrating, lubricating, and moisturizing shaving solution which comprises from about fifty percent by volume to about eighty percent by volume, and preferably about sixty percent by volume, of 1,2-propylene glycol in aqueous solution. The shaving solution of the present invention is applied to the area to be shaved prior to shaving, and is adapted to substitute for conventional shaving soaps or foams or more time-consuming prior art shaving preparations and techniques.

5 Claims, No Drawings

1,2-PROPYLENE GLYCOL SHAVING SOLUTION AND METHOD OF USE THEREOF

This is a continuation of copending application(s) Ser. No. 07/573,465 filed on Aug. 27, 1990 now abandoned.

FIELD OF THE INVENTION

The invention relates to an aqueous 1,2-propylene glycol shaving solution suitable as a substitute for conventional shaving soaps or foams or more time-consuming prior art shaving preparations and techniques.

BACKGROUND OF THE INVENTION

For conventional shaving with a safety razor or a straight razor, once the area to be shaved is wetted, a shaving soap or foam is applied in order to more fully hydrate the hairs. This procedure is followed both by males, when shaving the beard, and by women, when shaving legs, underarms, facial hair, or the bikini line. One disadvantage associated with shaving soaps and foams is that the hydration of the hairs is not complete, and thus they often do not lubricate well at the razor edge. The razor can tend to stick, leading to nicks, cuts, or skin irritation. In addition, the soaps or foams tend to desiccate the skin, and creams or emollients must often be applied after shaving to re-hydrate the skin.

In a prior art shaving system which attempts to increase hydration of the hairs, a 45% by volume 1,2-propylene glycol aqueous solution is first splashed on the area to be shaved. This helps to more fully hydrate the hairs. Then, after applying the 45% by volume 1,2-propylene glycol aqueous solution, a hot, wet towel is applied to the area to be shaved for one to two minutes in order to further increase hydration of the hairs. The 45% by volume 1,2-propylene glycol aqueous solution is then re-applied, followed by application of a shaving soap or foam. The area is then shaved.

However, in the prior art system referred to above, the additional required steps of applying the 45% by volume 1,2-propylene glycol aqueous solution twice and using a hot, wet towel make it more time consuming than using shaving soap or foam in the conventional manner.

SUMMARY OF THE INVENTION

The present invention includes a shaving solution with about fifty percent to about eighty percent by volume, and preferably about sixty percent by volume, of a 1,2-propylene glycol aqueous solution. This solution can be used as a substitute for conventional shaving preparations, including shaving soaps or foams and water, and for the 45% by volume 1,2-propylene glycol aqueous solution referred to above, in order to more fully hydrate the hairs to be shaved and provide lubrication and moisturization of the skin.

In use, the area to be shaved is flooded with the solution of the present invention. The solution of the present invention is preferably applied with an atomizer. The area is then shaved with a conventional safety or straight-edge razor. The solution of the present invention provides better hydration of the hairs and lubrication of the skin than is achieved by conventional methods, such as using a shaving foam or soap in combination with water. It also hydrates the hairs more fully than the above-described prior art method, in which the 45% by volume 1,2-propylene glycol aqueous solution is used in combination with a hot, wet towel and conventional shaving soap or foam. This enhanced hydration increases the ease with which a razor cuts through the hairs and reduces nicks and cuts, which makes the solution and system of the present invention well-suited for those suffering from mild forms of razor rash, or those having sensitive skin. Of course, persons who do not have such problems will also be pleased with the manner in which the present invention facilitates shaving.

DETAILED DESCRIPTION OF THE PREFERRED EMBODIMENT

The preferred shaving solution of the present invention is a sixty percent by volume aqueous solution of 1,2-propylene glycol. The 1,2-propylene glycol concentration can, however, vary from about fifty percent by volume to about eighty percent by volume. The solution can also contain additives, for example, scents, perfumes, or preservatives.

If the concentration of 1,2-propylene glycol is substantially less than about fifty percent by volume, hydration and lubrication are less than is desired, resulting in increased and unacceptable incidence of nicks and cuts. If the 1,2-propylene glycol concentration is greater that about eighty percent by volume, the solution tends to become oily and less effective as a hydrating agent because the water concentration becomes too low.

To use the solution of the present invention, the area to be shaved is flooded with it. It is preferable for the solution to be applied in atomized form, such as with a pump spray or similar apparatus. However, it could also be applied by other means, such as by splashing or pouring on the areas to be shaved. The skin is then shaved with a razor, and after shaving, the excess solution and cut hairs are wiped off the skin. There is no need to rinse the shaved area because the solution of the present invention moisturizes the skin and leaves it soft and moist. The solution of the present invention can also be used as a moisturizer in areas of the body that do not require shaving.

Because of its lubricating qualities, the shaving solution of the present invention is well suited for those who suffer from mild forms of razor bumps, otherwise known as pseudofolliculitis barbae ("PFB"). For more severe PFB cases, the system disclosed in U.S. Pat. No. 4,944,939 should be used. The present shaving solution is also recommended for use by those with milder forms of shaving irritation, such as razor rash, and for persons with sensitive skin.

It should be understood that the foregoing terms, expressions, and examples are exemplary only and not limiting, and that the scope of protection is defined only by the claims which follow and includes all equivalents of the subject matter of those claims.

What is claimed is:

1. A method of shaving a human skin area comprising the steps of:
    flooding the human skin area to be shaved with an aqueous solution consisting of from about fifty percent by volume to about eighty percent by volume of 1,2-propylene glycol in combination with water, as active ingredients; and
    shaving the flooded skin area.

2. The method of claim 1 wherein the solution is applied in atomized form.

3. The method of claim 2 wherein the solution is applied with a pump spray apparatus.

4. The method of claim 1 further including the step of wiping excess shaving solution and hairs from the shaved area.

5. A method of shaving a human skin area comprising the steps of:

flooding the human skin area to be shaved with an aqueous solution consisting of about sixty percent by volume of 1,2-propylene glycol in combination with water, as active ingredients; and shaving the flooded skin area.

* * * * *